United States Patent [19]  [11] 4,138,488
Sherlock et al.  [45] Feb. 6, 1979

[54] DIPHENYLMETHYL PICOLINIC ACID DERIVATIVES AND THEIR USE AS ANTI-ACNE AGENTS

[75] Inventors: Margaret H. Sherlock, Bloomfield; Heide Roebke, Belleville, both of N.J.

[73] Assignee: Schering Corporation, Kenilworth, N.J.

[21] Appl. No.: 758,297

[22] Filed: Jan. 10, 1977

Related U.S. Application Data

[63] Continuation-in-part of Ser. No. 636,009, Nov. 28, 1975, abandoned.

[51] Int. Cl.² .................. A61K 31/455; C07D 213/56
[52] U.S. Cl. .................................. 424/250; 424/266; 544/131; 544/365; 546/323; 546/314; 546/281; 546/194; 546/286; 546/326; 546/327; 546/301; 546/303; 546/290; 546/345; 546/346; 546/348; 546/349; 546/343; 260/244.4
[58] Field of Search .................. 424/266, 263, 295 R, 424/250; 260/295 R, 295 S, 295.5 R, 295.5 S; 544/365

[56] References Cited
U.S. PATENT DOCUMENTS
3,910,936  10/1975  Draber et al. .................... 260/295 S

*Primary Examiner*—Richard Raymond
*Attorney, Agent, or Firm*—Bruce M. Eisen; Raymond A. McDonald

[57] ABSTRACT

Disclosed herein are substituted diphenylmethyl picolinic acids, pharmaceutically acceptable salts, amides and esters thereof. The compounds disclosed are useful as topical anti-acne agents.

22 Claims, No Drawings

DIPHENYLMETHYL PICOLINIC ACID DERIVATIVES AND THEIR USE AS ANTI-ACNE AGENTS

CROSS REFERENCE TO RELATED APPLICATIONS

This application is a continuation-in-part of copending application Ser. No. 636,009, filed Nov. 28, 1975, now abandoned.

This invention relates to picolinic acids bearing diphenylmethyl or substituted diphenylmethyl substituents. More particularly, this invention relates to novel diphenylmethyl substituted picolinic acids, esters, amides and pharmaceutically acceptable salts thereof and to their use in the treatment and alleviation of acne.

The tangible embodiments of this invention are represented by the following structural formula:

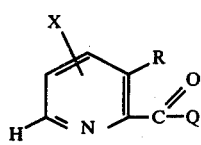

and the pharmaceutically acceptable salts thereof wherein X is a diphenylmethyl group having the structural formula:

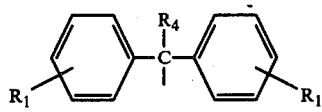

wherein $R_4$ is a member of the group consisting of hydrogen and lower alkyl; each $R_1$ is a member of the group consisting of hydrogen, halogen, hydroxy, alkyl, alkoxy, trifluoromethyl, and phenyl; Q is a member of the group consisting of hydroxy, alkoxy, cyanoalkoxy, glyceryl, $-NR_2R_3$, $-O$-alkylene-$NR_2R_3$, $-NR_2$-alkylene$-OH$; R is a member of the group consisting of hydrogen, lower alkyl and $X_1$, $X_1$ being defined the same as X; $R_2$ and $R_3$ which may be the same or different are members selected from the group consisting of hydrogen and alkyl or $R_2$ and $R_3$ together with the amido nitrogen atom may form a 5 to 7 membered ring which may contain a second heteroatom selected from the group consisting of oxygen and nitrogen; with the proviso that when R is other than hydrogen, X must be located at the 5-position of the pyridine ring.

As used herein the term "alkyl" means a straight, branched chain or cyclized hydrocarbyl having up to 12 carbon atoms. The term "alkoxy" means a straight, branched chain or cyclized hydrocarbyl which is bonded to an oxygen atom by a single bond. When such terms are modified by the term "lower" then such radicals contain up to six carbon atoms. Representative of the alkyl and alkoxy groups are methyl, ethyl, n-butyl, t-butyl, octyl, dodecyl, isopropyl, cyclopropyl, cyclopentyl, cycloheptyl, cyclooctyl, methoxy, ethoxy, n-butyloxy, t-butyloxy, octyloxy, dodecyloxy, isopropyloxy, cyclopropyloxy, cyclopentyloxy, cycloheptyloxy, cyclooctyloxy, and the like, with the lower alkyl and lower alkoxy groups being preferred.

The term "$-O$-alkylene-$NR_2R_3$", which is sometimes also described herein as "aminoalkyloxy", represents an alkylene group consisting of a divalent straight, branched or cyclized hydrocarbyl having up to 12 carbon atoms, which is between an oxygen atom and the $NR_2R_3$ group. Preferably, the alkylene moiety has up to six carbon atoms. Among the preferred "$-O$-alkylene-$NR_2R_3$" groups are: aminoethoxy, aminopropyloxy, mono and dialkylaminoethoxy, mono and dialkylaminovaleryloxy, piperidinoethoxy, morpholinoethoxy, piperazinoethoxy, pyrrolidinoethoxy, morpholinopropyloxy, morpholinovaleryloxy and piperazinoisopropyloxy.

Examples of groups represented by "$NR_2R_3$" are amino, mono and dialkylamino, morpholino, pyrrolidino, piperidino and piperazino.

In view of the foregoing definition of the terms "$NR_2R_3$" and "$O$-alkylene-$NR_2R_3$", the definition of the terms "$NR_2$-alkylene-$OH$" and "$O$-alkylene-$CN$" (cyanoalkoxy) are obvious.

The term "glyceryl" is the radical generally shown as $-OCH_2CHOHCH_2OH$.

Exemplary of the salts of the picolinic acid of Formula I, i.e. wherein "Q" represents hydroxy, are those formed with alkali metals, alkaline earth metals and non-toxic organic bases such as N-methyl glucamine and alcoholamines, preferably diethanolamine.

The compounds of this invention may be prepared by a series of reactions which individually are known to those skilled in the chemical art. The preferred reaction sequence by which the compounds of this invention having a diphenylmethyl substituent at the 5-position may be prepared is initiated by the reaction wherein a benzhydrol (II) is condensed with a 2-hydroxypyridine (III) to produce a substituted diphenylmethyl pyridone (IV). This condensation is effected by heating a mixture containing equimolar quantities of the reactants within the temperature range of about 225° C. to about 275° C. (preferably about 245° C.) in the presence of a strong acid, such as, for example, sulfuric acid. The pyridones (IV) are treated with a phosphorous oxyhalide reagent, e.g. phenylphosphonic dichloride, at an elevated temperature thereby forming the corresponding 2-halogeno pyridine (V). The 2-halogeno compound is converted to its 2-cyano analog (VI) by conventional means. The 2-cyano analog is then hydrolyzed to the corresponding substituted diphenylmethyl picolinic acid (Ia). The foregoing reactions are depicted by the following flow diagram:

Reaction Scheme I:

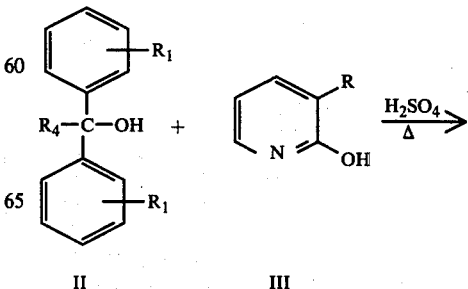

-continued

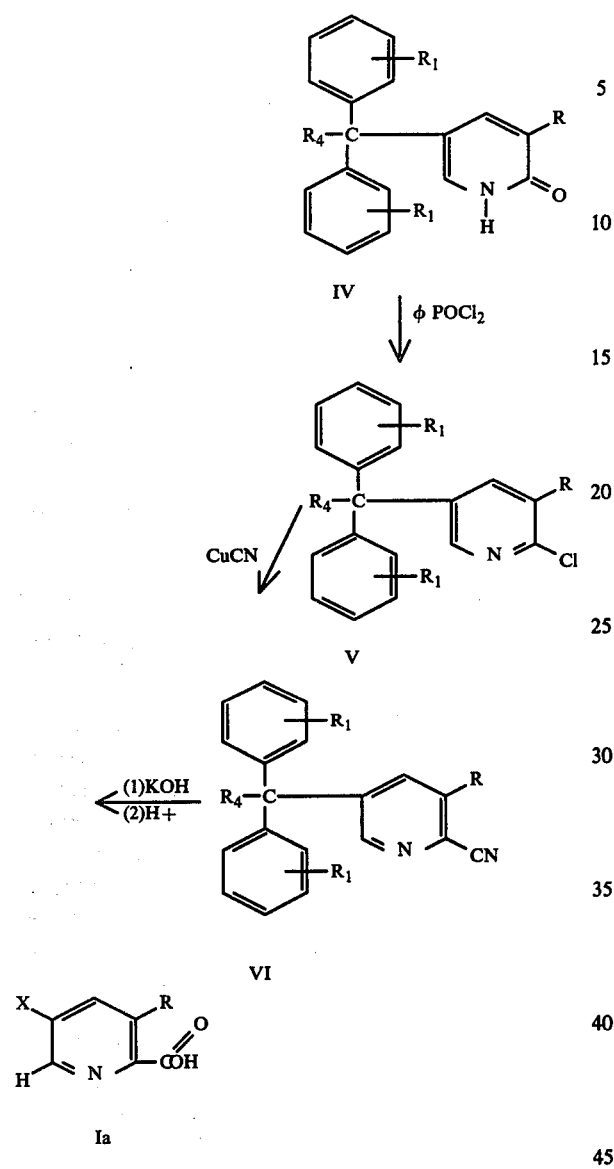

In the process described by the sequence set forth above, $R_1$, R, $R_4$ and X are as defined for formula I.

In the preferred method for preparing the compounds of this invention wherein R represents a substituted diphenylmethyl moiety, (i.e. those compounds of Formula I wherein both R and X are the same diphenylmethyl substituent), 2-hydroxypyridine is reacted with a benzhydrol (II) under substantially the same reaction conditions described for the preparation of compounds IV in Reaction Scheme I, except the reaction is effected at from about 150° to about 200° to favor the condensation of the benzhydrol (II) at the 1-position (i.e. on the nitrogen atom of the pyridine moiety). When a second mole of substituted benzhydrol is subsequently condensed with the first condensation product (VIII), the reaction is effected at a temperature in the range of from about 225° to about 275°. This reaction causes migration of the first benzhydryl moiety from the nitrogen atom, and the concomitant condensation of a second benzhydryl moiety to produce an appropriately substituted 3,5-[bis-(diphenylmethyl)]-2-hydroxypyridine (IX). The product is converted to the corresponding 3,5-[bis-(diphenylmethyl)]-picolinic acid (Ib) by substantially the same series of reactions described in Reaction Scheme I. These reactions are depicted in Reaction Scheme II.

Reaction Scheme II:

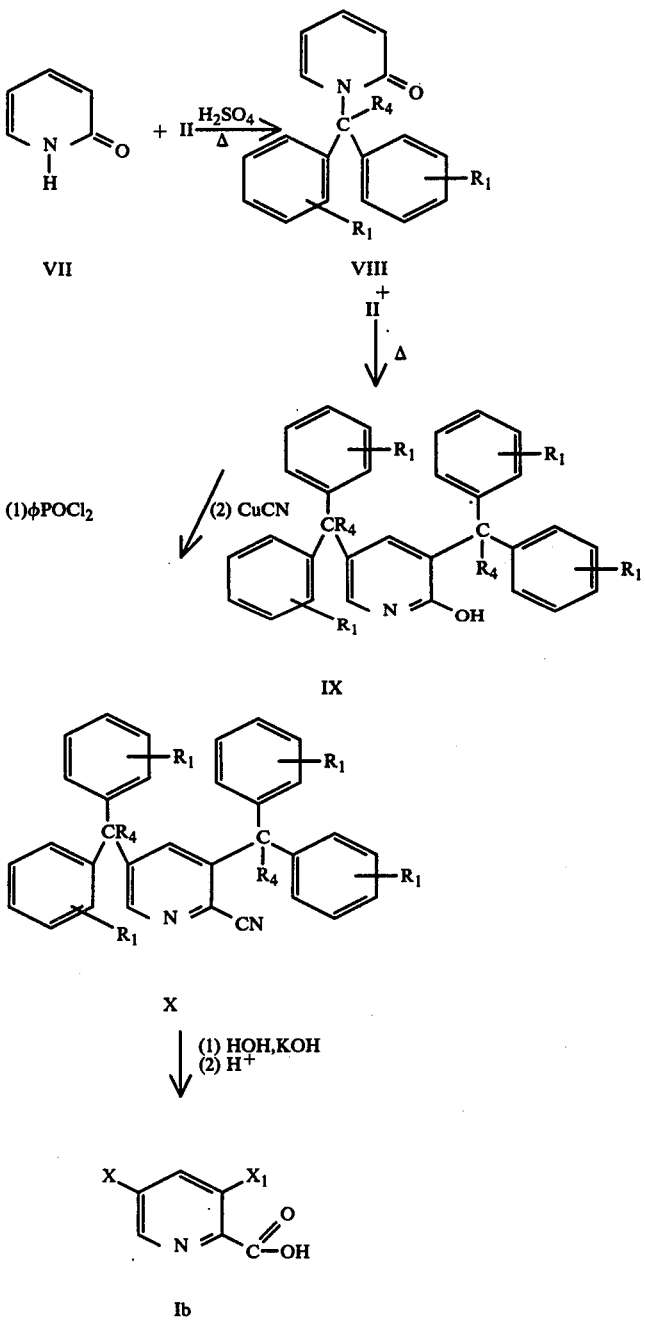

wherein X and $X_1$ are as previously defined.

In a preferred method for preparing the compounds of this invention having a diphenylmethyl or a substituted diphenylmethyl group at the 4-position of the picolinic acid moiety, 4-benzhydrylpyridinium sulfate salt (whose preparation is known in the art) is reacted with formamide in the presence of ferrous sulfate and a peroxide, preferably t-butylhydroperoxide, to form the corresponding 4-benzhydryl picolinamide (XII). The latter compound is then subjected to hydrolysis under acidic conditions thereby forming the 4-benzhydryl picolinic acid directly.

The foregoing reactions are depicted by the following flow diagram:

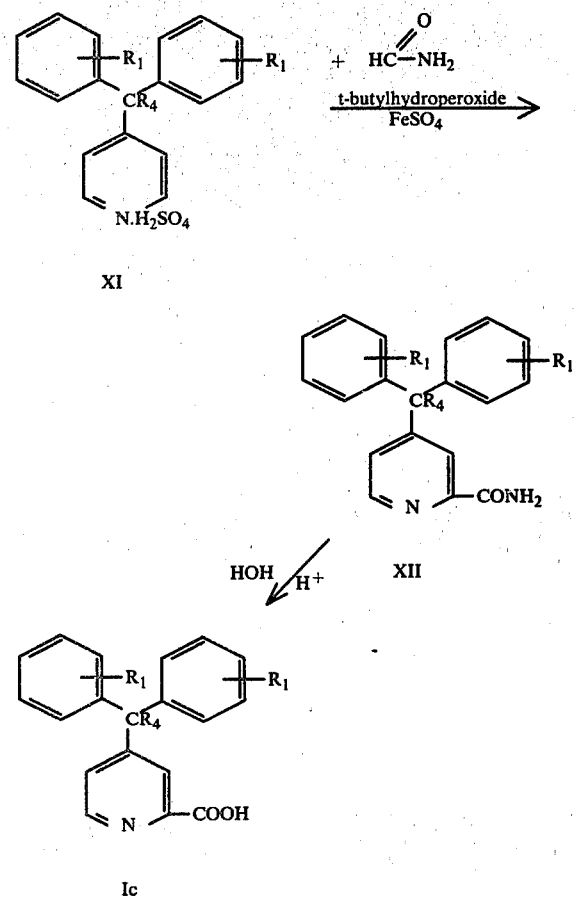

wherein $R_1$ and $R_4$ are as defined above.

To prepare the compounds of this invention wherein $R_4$ represents a lower alkyl radical, it is preferable first to alkylate a diphenylmethyl pyridine (XIII), and then follow the series of reactions set forth in Reaction Scheme III. The alkylation is effected in an inert solvent by reaction with a lower alkyl halide in the presence of sodium amide and excess ammonia, with ferric nitrate being present in catalytic quantities according to standard techniques known in the art. The foregoing reaction is depicted by the following reaction scheme:

Reaction Scheme IV:

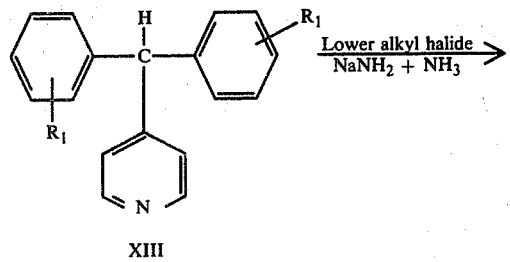

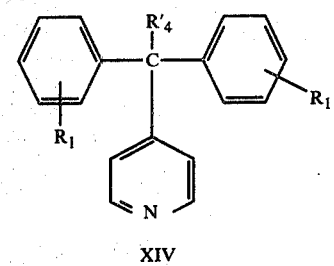

wherein $R_1$ is as previously defined and $R'_4$ is lower alkyl.

The amides and esters of this invention may conveniently be prepared from the acid (Ib) by first converting the acid to its cyanomethyl ester and then converting this ester to the desired end product by standard transesterification techniques.

Conversion of an R-substituted ($R_1$-diphenylmethyl)-picolinic acid to the corresponding cyanomethyl ester is usually effected by treating the acid at an elevated temperature with a halogenoacetonitrile in the presence of an acid acceptor, such as triethylamine. The reaction is, advantageously, effected in a non-reactive organic solvent such as acetone, methyl ethyl ketone, or the like. The reaction is allowed to proceed for from about 5 to about 20 hours, the reaction mixture is cooled and filtered. The filtrate is concentrated to a residue and triturated with water to yield the desired cyanomethyl ester. The cyanomethyl ester, is a key intermediate from which nearly all of the compounds having the various "Q" substitutents may be prepared. Indeed, from the cyanomethyl intermediate the compounds of this invention wherein "Q" represents glyceryl, alkoxy, —O-alkylene-$NR_2R_3$, —$NR_2R_3$ (except when $R_2$ and $R_3$ both represent hydrogen), and —$NR_2$— alkylene-OH may be prepared by the use of the transesterification and amidation techniques. Of course, in those instances wherein the transesterification process is designed to produce an amine having a reactive hydrogen, in such reactions the amine groups are first protected (e.g. by standard benzylation procedures) and subsequent to the transesterification, the benzyl or ether protective groups are readily cleaved by standard techniques well known in the art. Similarly, when "Q" represents a hydroxyalkylamine, the terminal hydroxy moiety must first be protected e.g. with a hydroxy (ether) protecting group and then following transesterification the protecting group removed. These procedures are conducted according to techniques well known in the art.

In those instances wherein it is desired to prepare amides wherein "$NR_2R_3$" is representative of $NH_2$, such R-substituted 5-($R_1$-diphenylmethyl)picolinamides may be prepared by hydrolysis of the corresponding R-substituted 5-($R_1$-diphenylmethyl)-2-cyanopyridine and may be isolated by conventional means.

To prepare compounds of this invention wherein Q is a glyceryl ester, several different routes may be utilized, the choice being determined by the ready availability of the required starting compounds. Preferentially, the ester is prepared by the hydrolysis of an alkylidenedioxypropyl ester of an appropriately substituted diphenylmethyl picolinic acid. The alkylidenedioxypropyl ester is generally prepared by transesterification wherein a reactive alkyl ester such as a cyanomethyl ester is transesterified by a cyclic acetal of glycerol. The transesterification is generally effected by heating the reactive ester with the cyclic acetal of glycerol in the presence of catalytic amounts of tertiary amine catalyst, such as triethylamine at temperatures in the range of 80°–200° C., about 100° C. being preferred. Due to the nature of the transesterification it is advantageous to employ a large excess of cyclic acetal to drive the reaction to completion. Hydrolysis of the alkylidenedioxypropyl ester of the R-substituted ($R_1$-diphenylmethyl)-picolinic acid to yield the desired glyceryl ester is usually effected by conventional techniques, such as by heating the intermediate in the presence of an acid. For example, by heating the intermediate in dilute acetic acid until the reaction is substantially complete and isolating the glyceryl ester by means known to the art.

The following specific examples are set forth to teach those skilled in the art how to prepare the compounds of this invention. They should not be construed as limiting the scope of the invention but rather to exemplify the generic teaching hereinabove.

EXAMPLE I

5-(Diphenylmethyl)-Picolinic Acid

A. 5-(diphenylmethyl)-2-pyridone

To a mixture of 92.1 g (0.5 mole) of benzhydrol and 142.7 g. (1.5 mole) of 2-hydroxypyridine heated at 180°, add with stirring 1.5 ml. of concentrated sulfuric acid. Heat the mixture at 250°–255° for 2 hours with the removal of water. Pour the cooled reaction mixture into water, stir, and extract with chloroform. Concentrate the chloroform extracts to a residue containing 5-(diphenylmethyl)-2-pyridone. Triturate the residue with ethyl acetate and filter the solids to obtain 5-(diphenylmethyl)-2-pyridone plus other isomers. Recrystallize from acetonitrile to obtain the product of this example, m.p. 174°–176° C.

In a similar manner, subject an equivalent quantity of the following $R_1$-substituted benzhydrols to the process of the foregoing step to obtain thereby the corresponding $R_1$-substituted diphenylmethyl-2-pyridones:

2-chlorobenzhydrol
4,4′-difluorobenzhydrol
4-phenylbenzhydrol
4-trifluoromethylbenzhydrol
3-methoxybenzhydrol, and
4,4′-dimethylbenzhydrol

B. 2-Chloro-5-(Diphenylmethyl)-Pyridine

Heat 55 g. of the crude 5-(diphenylmethyl)-2-pyridone and 110 ml. of phenylphosphoric dichloride at 200°–210° with stirring for 6 hours. Pour the cooled reaction mixture onto ice, basify with ammonium hydroxide, extract with ethyl ether, dry the ether extracts, and concentrate to a residue. Distill the residue at 160°–175°/0.15 mm. and crystallize the distillate from hexane to obtain 2-chloro-5-(diphenylmethyl)-pyridine, m.p. 69.5°–71°.

In a similar manner, subject an equivalent quantity of the following $R_1$-substituted diphenylmethyl-2-pyridones to the process of the foregoing step to obtain thereby the corresponding 2-chloro-($R_1$-substituted diphenylmethyl)-pyridines:

5-(2-chlorophenyl-phenylmethyl)-2-pyridone,
5-[bis-(4-fluorophenyl)-methyl]-2-pyridone,
5-(4-biphenyl-phenylmethyl)-2-pyridone,
5-(4-trifluoromethyl)phenyl-phenylmethyl)-2-pyridone,
5-(3-methoxyphenyl-phenylmethyl)-2-pyridone,
5-[bis-(4-methylphenyl)-methyl]-2-pyridone, and
5-(diphenylmethyl)-3-methyl-2-pyridone.

C. 5-(Diphenylmethyl)-Picolinic Acid

Heat a mixture of 16.5 g. (0.059 mole) of 2-chloro-5-(diphenylmethyl)-pyridine and 10.6 g. (0.059 mole) of cuprous cyanide in 120 ml. of hexamethylphosphoramide with stirring at 210°–220° C. for 7 hours. Pour the cooled reaction mixture into a solution of 200 ml. of ethylenediamine in 500 ml. of water, and extract with benzene. Wash the benzene extracts with 10% aqueous sodium cyanide, then with water, dry, treat with activated charcoal, filter, and concentrate to obtain 2-cyano-5-(diphenylmethyl)-pyridine. This compound is converted directly to the title compound by heating at reflux with 13 g. of potassium hydroxide pellets in 100 ml. water and 200 ml. ethylene glycol for 15 hours. Remove the ethylene glycol and water under reduced pressure, dissolve the residue in water, acidify with concentrated hydrochloric acid, and extract with chloroform. Dry the chloroform extracts. Concentrate the dried extracts to a residue and triturate the residue with isopropyl ether. Filter the solids, dry and recrystallize from ethanol to obtain 5-(diphenylmethyl)picolinic acid, m.p. 189°–191° C.

In a similar manner, subject an equivalent quantity of the following 2-chloro-($R_1$-substituted diphenylmethyl)-pyridines to the process of the foregoing step to obtain thereby the corresponding ($R_1$-substituted diphenylmethyl)-picolinic acids:

2-chloro-5-(2-chlorophenyl-phenylmethyl)-pyridine,
2-chloro-5-[bis-(4-fluorophenyl)-methyl]pyridine,
2-chloro-5-(4-biphenyl-phenylmethyl)-pyridine,
2-chloro-5-[4-(trifluoromethyl)-phenyl-phenylmethyl]-pyridine,
2-chloro-5-(3-methoxyphenyl-phenylmethyl)-pyridine,
2-chloro-5-[bis-(4-methylphenyl)-methyl]-pyridine, and
2-chloro-5-(diphenylmethyl)-3-methylpyridine.

EXAMPLE II

Cyanomethyl 5-(Diphenylmethyl)-picolinate

Suspend 4.3 g. (0.015 mole) of 5-(diphenylmethyl)-picolinic acid in 100 ml. of acetone with stirring and add 2.3 g. (0.023 mole) of triethylamine. To the resulting solution add dropwise 1.7 g. (0.023 mole) of chloroacetonitrile. Stir the reaction mixture at room temperature (25° C.) for 15 minutes, then reflux for 4 hours. Cool and filter the reaction mixture. Concentrate the filtrate to a residue in vacuo and triturate the residue with hot isopropyl ether to yield the product of this example, yield 3.5 g., m.p. 95°–98° C.

In a similar manner, subject an equivalent quantity of the following ($R_1$-substituted diphenylmethyl)-picolinic acids to the process set forth above to obtain thereby the corresponding cyanomethyl ($R_1$-substituted diphenylmethyl) picolinates:

5-(2-chlorophenyl-phenylmethyl)-picolinic acid,
5-[bis-(4-fluorophenyl)-methyl]-picolinic acid,
5-(4-biphenyl-phenylmethyl)-picolinic acid,
5-[4-(trifluoromethyl)-phenyl-phenylmethyl)-picolinic acid,
5-(3-methoxyphenyl-phenylmethyl)-picolinic acid,
5-[bis-(4-methylphenyl)-methyl]-picolinic acid, and 5-(diphenylmethyl)-3-methylpicolinic acid

EXAMPLE III

5-(4-Chlorophenyl-Phenylmethyl)-Picolinic Acid

A. 5-(4-Chlorophenyl-Phenylmethyl)-2-Pyridone

Combine 109.3 g. (0.5 mole) of 4-chlorobenzhydrol with 142.7 g. (1.5 mole) of 2-hydroxypyridine and heat at 150° C. with stirring until molten. Add about 2 ml. of concentrated sulfuric acid and continue heating to 240°-250° C. while removing water from the reaction mixture. Permit the reaction to continue for about 2 hours, then cool the reaction mixture to about 25° C. Treat the resulting solid with ethyl acetate and water and filter to remove the undesired 3-(4-chlorophenyl-phenylmethyl)-2-pyridone. The organic layer is separated and washed with water several times and dried over potassium carbonate and filtered. Concentrate the filtrate to half volume and filter to remove the remaining 3-substituted-2-pyridone. Evaporate the filtrate and dissolve the residue in ethyl ether. Upon standing overnight the 5-(4-chlorophenyl-phenylmethyl)-2-pyridone crystallizes, yield 60 g., m.p. 164°-169° C.

B. 2-Chloro-5-(4-Chlorophenyl-Phenylmethyl)-Pyridine

Combine 50 g. (0.174 mole) of the 5-substituted 2-pyridone from step A with 125 ml. of phenylphosphonic dichloride and heat at 210°-220° C. for about 7 hours with stirring. Allow to stand overnight and pour onto ice. Basify with ammonium hydroxide and extract with ethyl ether. Dry the ether solution and concentrate to a residue. Distill the residue and collect the fraction boiling at 205°-215° C. at 0.55 mm. (49 g.).

C. 5-(4-Chlorophenyl-Phenylmethyl)-Picolinic Acid

Dissolve 55 g. of the product of step B in 200 ml. of dry hexamethylphosphoramide and add 32 g. (0.36 mole) of cuprous cyanide. Heat the reaction mixture at 210°-220° C. for 7 hours. Pour the reaction mixture into about 500 ml. of ice water containing 200 ml. of ethylenediamine and extract with benzene. Wash the benzene extract with 10% sodium cyanide solution then with water. Treat the benzene solution with activated charcoal and filter through a suitable filter aid. Evaporate the filtrate to dryness, dissolve the residue in 300 ml. of ethylene glycol and add 20 g. of potassium hydroxide dissolved in 100 ml. of water. Reflux the reaction mixture overnight and remove the solvent in vacuo. Dissolve the residue in water, treat with activated charcoal and filter. Acidify the filtrate with concentrated hydrochloric acid, extract the precipitate thus formed with chloroform and evaporate the extract to a residue. Triturate the residue with acetonitrile and obtain thereby the product of this example, m.p. 200°-203° C.

EXAMPLE IV

3,5-Bis-(Diphenylmethyl)-Picolinic Acid

A. N-Diphenylmethyl-2-pyridone

Combine 92.1 g (0.5 mole) of benzhydrol with 142.7 g. (1.5 mole) of 2-hydroxypyridine and heat to 190° C. with stirring. Add 1.5 ml. of concentrated sulfuric acid and follow the procedure of Example III, step A to obtain thereby the product of this step yield 68 g., m.p. 142°-145° C.

In a similar manner, subject an equivalent quantity of the following $R_1$-substituted benzhydrols to the process set forth above to obtain thereby the corresponding N-substituted-2-pyridone:

4-chlorobenzhydrol,
4,4'-dichlorobenzhydrol,
2-chlorobenzhydrol,
4,4'-difluorobenzhydrol,
4-phenylbenzhydrol,
4-trifluoromethylbenzhydrol,
3-methoxybenzhydrol, and
4,4'-dimethylbenzhydrol

B. 3,5-Bis-(Diphenylmethyl)-2-pyridone

Combine 46 g. (0.18 mole) of N-substituted-2-pyridone with 33.2 g. (0.18 mole) of benzhydrol and heat to 230° C. Add about 1 ml. of concentrated sulfuric acid and heat at 250°-260° C. for about 2 hours. Cool the reaction mixture to about 25° C. and stir the solid reaction product with hot acetonitrile, filter, wash and dry to obtain thereby the product of this step, yield 49 g., m.p. about 240° C.

In a similar manner, subject an equivalent quantity of the following N-substituted-($R_1$-substituted diphenylmethyl)-2-pyridones to the process set forth above with the appropriately substituted benzhydrol to obtain thereby the corresponding 3,5-bis-($R_1$-substituted-diphenylmethyl)-2-pyridones:

N-(4-chlorophenyl-phenylmethyl)-2-pyridone,
N-[bis-(4-chlorophenyl)-methyl]-2-pyridone,
N-(2-chlorophenyl-phenylmethyl)-2-pyridone,
N-[bis-(4-fluorophenyl)-methyl]-2-pyridone,
N-(4-biphenyl-phenylmethyl)-2-pyridone,
N-[4-(trifluoromethyl)-phenyl-phenylmethyl]-2-pyridone,
N-(3-methoxyphenyl-phenylmethyl)-2-pyridone, and
N-[bis-(4-methylphenyl)-methyl]-2-pyridone,

C. 2-Chloro-3,5-bis-(diphenylmethyl)-pyridine

Combine 49.5 g. (0.11 moles) of 3,5-bis-(diphenylmethyl)-2-pyridone (prepared as described in step B) with 105 ml. of phenylphosphonic dichloride and heat the reaction mixture with stirring at 200°-210° C. for 6 hours. Pour the reaction mixture onto ice and basify with ammonium hydroxide. Extract with ethyl ether, dry the extract and evaporate to yield a residue which is crystallized from ethanol to yield the product of this step, yield about 40 g., m.p. 131°-133° C.

In a similar manner, subject an equivalent quantity of the following 3,5-bis-($R_1$-substituted diphenylmethyl)-2-pyridones to the process set forth above to obtain thereby the corresponding 2-chloro-3,5-bis-($R_1$-substituted diphenylmethyl)-pyridines:

3,5-bis-(4-chlorophenyl-phenylmethyl)-2-pyridone,
3,5-bis-[bis-(4-chlorophenyl)-methyl]-2-pyridone,
3,5-bis-(2-chlorophenyl-phenylmethyl)-2-pyridone,
3,5-bis-[bis-(4-fluorophenyl)-methyl]-2-pyridone,
3,5-bis-(4-biphenyl-phenylmethyl)-2-pyridone,
3,5-bis-[4-(trifluoromethyl)-phenyl-phenylmethyl]-2-pyridone,
3,5-bis-(3-methoxyphenyl-phenylmethyl)-2-pyridone, and
3,5-bis-[bis-(4-methylphenyl)-methyl]-2-pyridone.

D. 3,5-Bis-(Diphenylmethyl)-Picolinic Acid

Combine 38.4 g. (0.086 mole) of 2-chloro-3,5-bis-(diphenylmethyl)-pyridine (as prepared in step C) with 15.3 g. (0.17 mole) of cuprous cyanide in 180 ml. of dry hexamethylphosphoramide. Heat the reaction mixture at 210°–220° C. for 7 hours. Pour the reaction mixture into aqueous ethylenediamine, extract with benzene, wash the benzene extracts with 10% sodium cyanide then with water and dry over potassium carbonate. Filter and concentrate the filtrate to a residue. Dissolve the residue in 300 ml. of ethylene glycol, add a solution of 15 g. potassium hydroxide in 90 ml. of water and reflux for about 22 hours. Concentrate the reaction mixture to a residue in vacuo and acidify the residue with dilute hydrochloric acid. Extract with benzene, and concentrate the solution to a residue containing the title product which was purified by conversion to the diethanolamine salt followed by regeneration of the acid, m.p. 172°–175° C.

In a similar manner, subject an equivalent quantity of the following 2-chloro-3,5-bis-($R_1$-substituted diphenylmethyl)-pyridines to the process set forth above to obtain thereby the corresponding 3,5-bis-($R_1$-substituted diphenylmethyl)-picolinic acids:

2-chloro-3,5-bis-(4-chlorophenyl-phenylmethyl)-pyridine,
2-chloro-3,5-bis-[bis-(4-chlorophenyl)-methyl]-pyridine,
2-chloro-3,5-bis-(2-chlorophenyl-phenylmethyl)-pyridine,
2-chloro-3,5-bis-[bis-(4-fluorophenyl)-methyl]-pyridine,
2-chloro-3,5-bis-(4-biphenyl-phenylmethyl)-pyridine,
2-chloro-3,5-bis-[4-(trifluoromethyl)-phenyl-phenylmethyl]-pyridine,
2-chloro-3,5-bis-(3-methoxyphenyl-phenylmethyl)-pyridine, and
2-chloro-3,5-bis-[bis-(4-methylphenyl)-methyl]-pyridine.

EXAMPLE V

4-(Diphenylmethyl)-Picolinic Acid

A. 4-(Diphenylmethyl)-Picolinamide

Dissolve 20 g. (0.082 mole) of 4-benzhydrylpyridine in 200 ml. of formamide and, with external cooling, add 4.35 ml. (0.082 mole) of sulfuric acid. Adjust the reaction temperature to 5°–10° C. while adding 21.6 g. (0.24 mole) of t-butyl hydroperoxide and 67 g. (0.24 mole) of ferrous sulfate over a 30 minute interval. Remove the iron salts by filtration. Wash the precipitate with chloroform and water and separate the two liquid phases. Extract the aqueous phase with chloroform, wash the combined chloroform phases with water and dry. Concentrate the extract to a residue, dissolve the residue in ether, filter and obtain the product of this step from the ether solution, yield 3.5 g., m.p. 165°–170° C. Additional product may be obtained by extracting the iron salts with refluxing chloroform.

In a similar manner, subject an equivalent quantity of the following 4-($R_1$-substituted diphenylmethyl)-pyridines to the process set forth above to obtain thereby the corresponding 4-($R_1$-substituted diphenylmethyl)-picolinamides:

4-(4-chlorophenyl-phenylmethyl)-pyridine,
4-[bis-(4-chlorophenyl)-methyl]-pyridine,
4-(2-chlorophenyl-phenylmethyl)-pyridine,
4-[bis-(4-chlorophenyl)-methyl]-pyridine,
4-(4-biphenyl-phenylmethyl)-pyridine,
4-[4-(trifluoromethyl)-phenyl-phenylmethyl]-pyridine,
4-(3-methoxyphenyl-phenylmethyl)-pyridine, and
4-[bis-(4-methylphenyl)-methyl]-pyridine.

B. 4-(Diphenylmethyl)-Picolinic Acid

Dissolve 5.3 g. of 4-(diphenylmethyl)-picolinamide (prepared in step A) in 80 ml. of concentrated hydrochloric acid and heat to reflux. Continue to reflux the reaction mixture overnight. Remove 50 ml. of the solvent by distillation in vacuo, treat the residue with ice and basify with excess 10% sodium hydroxide. Add 300 ml. of water and extract the solution with 50 ml. of ethyl ether. Adjust the pH of the aqueous phase to about 5, recover the precipitate by filtration and dry to obtain thereby the product of this example, m.p. 172°–177° C. Crystallize the product from 75 ml. of acetonitrile, yield 3.8 g., m.p. 176°–178° C.

In a similar manner, subject an equivalent quantity of the following 4-($R_1$-substituted diphenylmethyl)-picolinamides to the process set forth above to obtain thereby the corresponding 4-($R_1$-substituted diphenylmethyl)-picolinic acids:

4-(4-chlorophenyl-phenylmethyl)-picolinamide,
4-[bis-(4-chlorophenyl)-methyl]-picolinamide,
4-(2-chlorophenyl-phenylmethyl)-picolinamide,
4-[bis-(4-chlorophenyl)-methyl]-picolinamide,
4-(4-biphenyl-phenylmethyl)-picolinamide,
4-[4-(Trifluoromethyl)-phenyl-phenylmethyl]-picolinamide,
4-(3-methoxyphenyl-phenylmethyl)-picolinamide, and
4-[bis-(4-methylphenyl)-methyl]-picolinamide.

EXAMPLE VI

5-[Bis-(4-Chlorophenyl)-methyl]-Picolinic Acid

A. 5-[Bis-(4-Chlorophenyl)-Methyl]-2-Pyridone

Combine 50.6 g. (0.2 mole) of 4,4'-dichlorobenzhydrol with 57.1 g. (0.6 mole) of 2-hydroxy pyridine, with stirring heat to 200° C. and add dropwise 1.0 ml. of concentrated sulfuric acid. Increase the reaction temperature to 240°–250° C. and maintain at that temperature range while collecting water emanating from the reaction. Cool the reaction mixture, add a mixture of ethyl acetate and water with stirring and separate the liquid phases. Dry the organic phase, reduce the volume of ethyl acetate, cool to precipitate the crude product, yield 43 g. Crystallization from ethanol affords the product of this step, m.p. 211°–215° C.

B. 2-Chloro-5-[Bis-(4-Chlorophenyl)-Methyl]-Pyridine

To a mixture of 35.2 g. (0.11 mole) of 5-[bis-(4-chlorophenyl)-methyl]-2-pyridone and 11.8 g. (0.11 mole) of 2,4-lutidine, add 50.6 g. (0.33 mole) of phosphorous oxychloride (dropwise) while heating the reaction mixture at 80°. Then, heat the reaction mixture at 120° C. for six hours. Pour the reaction mixture onto ice, basify with ammonium hydroxide, extract with benzene and remove both the benzene and residual 2,4-lutidine by distillation. Distill the residue at about 195°–210° C. (0.01 mm) to obtain thereby about 30 g. of the product of this step as a yellow viscous oil.

C. 5-[Bis-(4-Chlorophenyl)-Methyl]-Picolinic Acid

Dissolve the product of step B above in about 150 ml. of dry hexamethylphosphoramide, add 15.4 g. (0.172 mole) of cuprous cyanide and follow the procedure described in Example IV, step D to obtain the product of this example.

EXAMPLE VII

5-(4-Chlorophenyl-Phenylmethyl)-Picolinic Acid Diethanolamine Salt

Combine 0.97 g. of 5-(4-chlorophenyl)-phenylmethyl)-picolinic acid (see Example IIIC) with 0.4 g. of diethanolamine in 100 ml. of ethyl acetate. Heat the reaction mixture and decant solvent from the brown insoluble residue. Upon standing, the product of this example precipitates from the ethyl acetate solution, m.p. 108°-115° C.

EXAMPLE VIII

5-[Bis-(4-Chlorophenyl)-Methyl]-Picolinic Acid Piperazine Salt

Combine 19.8 g. (0.055 mole) of 5-[bis-(4-chlorophenyl) methyl]-picolinic acid with 4.7 g. of piperazine in hot methanol. Add 5 volumes of ether and collect the precipitate by filtration. Recrystallize the precipitate from ethanol to obtain thereby the product of this example, m.p. 240°-255° C.

The processes described in the last two examples, or either of them, may be used to prepare pharmaceutically acceptable salts of the compounds of this invention. Alternatively, other processes known in the art may be utilized in lieu thereof.

EXAMPLE IX

4-(1,1-Diphenylpropyl)-Picolinic Acid

A. 4-(1,1-Diphenylpropyl)-Pyridine

Dissolve 2.5 g. of sodium in 500 ml. of liquid ammonia in the presence of a catalytic amount of ferric nitrate. Add dropwise to the resulting suspension over a 20 minute interval a solution containing 24.5 g. of 4-diphenylmethyl pyridine in 600 ml. of ether. Stir the resulting dark red mixture for an additional 20 minutes, then add 13 g. of ethyl bromide dropwise. Add an additional 500 ml. of ammonia, stir overnight, then add 300 ml. of ether followed by 150 ml. of water. Separate the solvent layers. Wash the ether layer with water until neutral, dry and remove the solvent under reduced pressure to a residue. Distill the residue at 192°-200° C./1.6 to 2 mm. and obtain thereby 14.7 g. of the title compound as an orange colored oil.

B. 4-(1,1-Diphenylpropyl)-Picolinamide

Subject the 4-(1,1-diphenylpropyl)-pyridine prepared in step A to the process of Example V, step A and obtain thereby 13.9 of a yellow oil which may be crystallized from acetonitrile to yield the title product, m.p. 144°-147° C.

C. 4-(1,1-Diphenylpropyl)-Picolinic Acid

Dissolve 3.8 g. of 4-(1,1-diphenylpropyl)-picolinamide in 50 ml. of ethanol, add 100 ml. of 10% aqueous potassium hydroxide and heat the resulting mixture at reflux overnight. Remove the ethanol under reduced pressure, add water to the residue and adjust to about pH 5 with 10% aqueous hydrochloric acid. Filter the resulting solid and crystallize the precipitate from ethanol to obtain thereby the compound of this example, yield — 1.6 g., m.p. 191°-193° C.

EXAMPLE X

5-(Diphenylmethyl)-Picolinic Acid

A mixture of 8.2 g. 2-styryl-5-(diphenylmethyl)-pyridine and 120 ml. of acetone is cooled to −10° C. and with vigorous stirring 6.66 g. of finely divided potassium permanganate is added slowly, in a portion-wise fashion, over a 1.5 hour period whilst maintaining the temperature below −5° C. Allow the mixture to stand at −15° C. for 15 hours, filter and wash the solids with chloroform and extract three times with 150 ml. of boiling water. Acidify the aqueous extracts with hydrochloric acid and extract with ether. Discard the ether extracts and basify the aqueous phase to pH 2.5 and filter and dry the precipitated acid which is recrystallized from ethanol to yield the tiltle product (m.p. 189°-191° C.).

EXAMPLE XI

5-(Diphenylmethyl)-Picolinic Acid 18 g. 2-methyl-5-(diphenylmethyl) pyridine, 1 liter of water, 9 g. of potassiumpermanganate are heated on a steam bath for about 3 hours until the reaction mixture is colorless. 9 g. of potassiumpermanganate, 200 milliliters of water are added and the reaction mixture is heated for about 5 hours until colorless. Filter and wash thoroughly with hot water (70°-90° C.), combine the filtrate and washes, cool to about 25° C., acidify with hydrochloric acid, and recover the 5-(diphenylmethyl)-picolinic acid by filtration (m.p. 189°-191° C.).

Acne is a common inflammatory disease in areas where sebaceous glands are largest, most numerous, and most active. It is characterized by the appearance of comedones, pustles, papules, inflammed nodules, and in extreme cases infected sacs. In the more inflammatory types of acne, *Corynebacterium acnes* and *Staphylococcus albus* are usually among the infecting organisms. It is believed that these organisms aggravate the existing inflammatory condition by releasing enzymes (lipase) which break down the lipid in the sebum with the concomitant release of irritating fatty acids. Thus, an effective anti-acne agent ought be one which can prevent or substantially reduce the breakdown of lipid in the sebum thereby exerting an anti-inflammatory effect upon the skin. Ideally, the anti-acne agent should be effective topically in order to minimize the advent of untoward side effects which may occur during systemic treatment. For instance, the more frequently used anti-acne agents, the tetracyclines are believed to be causally related to side effects which appear with the long term systemic treatment usually required in treating acne. These adverse effects include gastrointestinal irritation, photosensitivity reactions, dizziness, nausea and vomiting. Thus, there is need for effective topically applied anti-acne agents. The compounds of this invention fill such a need.

When tested in vitro by a slightly modified version of the test procedure described by A. Shalita and V. Wheatley, in J. Invest, Dermatol. 54, 413 (1970), the compounds of this invention were shown to substantially inhibit the formation of free fatty acids from triglycerides by bacterial lipases, including those formed by *Corynebacterium acnes*. The free fatty acids produced were assayed by the automated colorimetric method of C. Dalton and C. Kowalski as described in Clinical Chem. 13, 744 (1967). Further, the test results clearly demonstrate that the anti-lipase activity of the compounds of this invention is substantially greater than that of hexachlorophene, or that of tetracycline. Additionally, neither hexachlorophene nor tetracycline exhibit substantial in vivo topical activity whereas the compounds of this invention do. Moreover, the instant compounds are substantially devoid of overt skin irritation upon repeated topical administration. They also exhibit little systemic toxicity following repeated topical application or upon systemic dosing via oral or intraperitoneal administration.

As mentioned, the compounds of this invention are effective antibacterial agents, particularly against *Corynebacterium acnes* and *S. albus*. Additionally, the compounds of this invention are effective against other gram-positive organisms and they also are antitrichomonal; they being particularly effective against *T. vaginalis*. As such, the compounds may be used in the conventional manner for treating gram-positive infections and for treating trichomonal infections. Potency assays and formulations for such uses utilize standard techniques.

The compounds of this invention are administered topically in pharmaceutical compositions having the conventional excipients. The compositions may be in the form of lotions, creams, aerosols and ointments. In these compositions, the active compound is present in the range of from about 0.5% to about 10% by weight, administration being from about 2 to about 5 times daily.

As is generally the case wherein a family of compounds exhibit a particular utility, certain members are preferred over others. In the instant invention, a preferred group of compounds are those wherein R is hydrogen or $X_1$, $R_1$ is hydrogen or halogen and Q is hydroxy including the pharmaceutically acceptable salts thereof. Particularly preferred are the compounds wherein $R_1$ is chloro and R is hydrogen. Another preferred group of compounds are those wherein $R_1$ is hydrogen, R is $X_1$, and Q is hydroxy, including the pharmaceutically acceptable salts thereof.

Yet another preferred group of compounds within the family defined by formula I are those wherein R and $R_1$ are as defined in said claim and Q is a member selected from the group consisting of polyhydroxyalkoxy, aminoalkyoxy. Particularly preferred are those compounds wherein the polyhydroxyalkoxy group in combination with the carbonyl to which it is attached forms a glyceryl ester.

The compounds of this invention tested by the in vitro test procedures set forth herein below:

A. In Vitro Test

1. Isolation of Organisms:

a. *C. acnes* organisms were obtained by gently squeezing the nasal surface of normal human volunteers. The expressed material was streaked across the surface of a Brain Heart Infusion Agar Plate and plates were incubated anaerobically at 37° C. for 7 days.

After 7 days the plates were examined and appropriate colonies were restreaked on blood agar to obtain isolated colonies. These plates were incubated aerobically for 28 hours. Suitable colonies were identified using gram staining. Those colonies positively identified as *C. acnes* were used to innoculate thioglycolate (10% glycerol) broth. After 7 days anaerobic incubation, the cultures were either frozen at −4° C. for future use or used to innoculate a Brain Heart Infusion broth for immediate use as follows: After 7 days the cells were separated from the Brain Heart Infusion broth by centrifugation (10,000 rpm for 30 minutes at 4° C.). The cells were discarded and the broth used to prepare the enzyme.

2. Enzyme Preparation

A known volume of broth was added very slowly with mixing to chilled acetone (4° C.) in a ratio of 1 volume broth to 1.5 volumes acetone.

The mixture was kept at −4° C. for ½ hour before filtering through a Buchner funnel using Whatman No. 1 paper.

The precipitate was saved and redissolved in 1/5 its original volume of $H_2O$ and lyophilized to yield the crude enzyme powder. This enzyme preparation is stable at −4° C. for at least 6 months.

3. Fatty Acid Free Olive Oil

Ten ml. of olive oil was extracted with 10 ml. of anhydrous ether in a 250 ml. separatory funnel together with 10 ml. of 10% $Na_2CO_3$. The mixture was shaken well, pressure released and then allowed to stand until the layers separate. The bottom layer was discarded and the washing with $Na_2CO_3$ repeated 4 more times. After discarding the bottom layer the remaining solution was placed in a beaker over a boiling water bath to remove all traces of ether (2-3 hours). One-tenth of gram of benzoic acid, 2.5 g. gum acacia, and 90 ml. hot water were added to the washed olive oil and blended in an homogenizer for 1 minute at high speed. The mixture is stable at 4° C. for 6 weeks.

Test Procedure

In Vitro

Corynebacterium Acnes Lipase (Primary Screen)

Semi-purified bacterial enzyme (prepared as described above) 0.15 ml. of a 50 mg/ml. solution is allowed to react with 0.1 ml. of 10% fatty acid free olive oil solution in a 2 ml total volume at a pH of 7.0 (0.2 phosphate buffer) and at 37° C. in an incubation vial. At the end of 3 hours, 0.3 ml of the reaction mixture is removed for free fatty acid (FFA) analysis. The activity of the enzyme preparation is expressed in terms of microequivalents ($\mu$eq) of FFA/liter of product.

*Staphylococcus aereus* Lipase

The assay conditions for this enzyme are the same as above except that the enzyme concentration is 5 mg/ml.

System for Determination of In Vitro Bacterial Lipase Inhibition

Test compounds ($5 \times 10^{-4}M \rightarrow 5 \times 10^{-8}M$) are added to the incubation vial in buffered solution, maintaining a final volume of 2 ml. Water insoluble compounds were first solubilized with an appropriate solvent ($CHCl_3$, DMSO) and an aliquot added to the vial the solvent evaporated under $N_2$ before addition of enzyme, substrate and buffer. Appropriate drug blanks without enzyme were included to assess any drug interference in the FFA assay. Incubation conditions and FFA analysis were the same as cited previously.

$$\% \text{ Inhibition} = \frac{(\text{Lipase Activity} - \text{Drug Lipase Activity})}{\text{Lipase Activity}} \times 100$$

The $IC_{50}$ for the test compounds is calculated using least squares regression from results obtained by testing a number of different molar drug concentrations giving inhibition ranging from 20–80%.

The following examples (i.e. Examples X through XIV inclusive) are directed to topical formulations in which the compounds of this invention may be utilized to elicit an antiacne response. The formulations are prepared by methods known in the art using the active compound in the form of an "micronized" solid.

EXAMPLE X

| Ointment | mg/gm |
| --- | --- |
| 5-(Diphenylmethyl)-Picolinic Acid | 20.0 |
| Propylene Glycol U.S.P. | 40.0 |
| Mineral Oil, U.S.P. | 50.0 |
| White Petrolatum, U.S.P. to make | 1.0 g. |

EXAMPLE XI

| Ointment | mg/gm |
| --- | --- |
| 3,5-[Bis-(Diphenylmethyl)-Picolinic Acid | 20.0 |
| Propylene Glycol, U.S.P. | 40.0 |
| Stearyl Alcohol, U.S.P. | 50.0 |
| Polyethylene Glycol 400, U.S.P. | 600.0 |
| Polyethylene Glycol 4000, U.S.P. to make | 1.0 g. |

EXAMPLE XII

| Gel | mg/gm |
| --- | --- |
| 4-(Diphenylmethyl)-Picolinic Acid | 20.0 |
| Propylene Glycol, U.S.P. | 300.0 |
| Polyethylene Glycol, 400 U.S.P. | 660.0 |
| Butylated Hydroxytoluene | 5.0 |
| Carbopol 940P | 15.0 |
| Titanium Dioxide, U.S.P. | 10.0 |
| Sodium Hydroxide, U.S.P. | 0.7 |

EXAMPLE XIII

| Cream | mg/gm |
| --- | --- |
| 5-(4-Chlorophenyl-Phenylmethyl)-Picolinic Acid | 20.0 |
| Stearic Acid, U.S.P. | 60.0 |
| Glyceryl Monostearate, Cosmetic | 100.0 |
| Propylene Glycol, U.S.P. | 50.0 |
| Polyoxyethylene Sorbitan Monopalmitate, Cosmetic | 50.0 |
| Sorbitol Solution, U.S.P. | 30.0 |
| Benzyl Alcohol, N.F. | 10.0 |
| Purified Water, U.S.P., to make | 1.0 gm. |

EXAMPLE XIV

| Glycol Ointment | mg/gm |
| --- | --- |
| 5-[Bis-(4-Chlorophenyl)-Methyl]-Picolinic Acid | 20.0 |
| Propyl Glycol Monostearate | 20.0 |
| Propylene Glycol, U.S.P. | 100.0 |
| White Wax U.S.P. | 60.0 |
| White Petrolatum q.s. to make | 1.0 gm. |

We claim:
1. A compound of the formula:

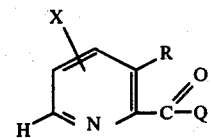

and the pharmaceutically acceptable salts thereof wherein X is a diphenylmethyl group having the structural formula:

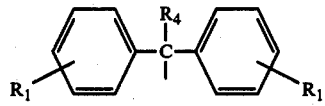

wherein $R_4$ is a member of the group consisting of hydrogen and lower alkyl; each $R_1$ is a member of the group consisting of hydrogen, halogen, hydroxy, alkyl, cycloalkyl, alkoxy, cycloalkoxy, trifluoromethyl and phenyl; Q is a member selected from the group consisting of hydroxy, alkoxy and glyceryl; R is a member of the group consisting of hydrogen, lower alkyl and $X_1$, $X_1$ being defined the same as X; wherein the alkyl, cycloalkyl, alkoxy and cycloalkoxy groups have up to 12 carbon atoms, the lower alkyl groups having 1 to 6 carbon atoms, said alkyl, lower alkyl and alkoxy groups including straight chain and branched chain hydrocarbyl groups; with the proviso that when R is other than hydrogen, X must be located at the 5-position of the pyridine ring.

2. A compound of claim 1 of the formula:

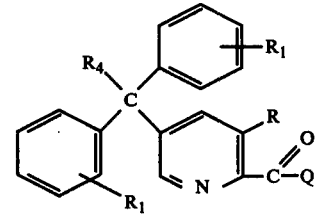

3. A compound of claim 1 of the formula:

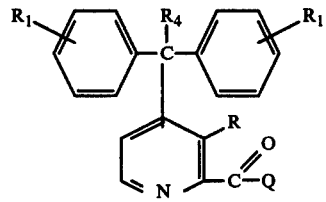

4. A compound of claim 2 wherein R and $R_4$ are hydrogen.

5. The compound of claim 4 wherein each $R_1$ is hydrogen and Q is hydroxy, said compound being 5-(diphenylmethyl)picolinic acid.

6. A compound of claim 4 wherein one of $R_1$ is a halogen the other $R_1$ being hydrogen.

7. The compound of claim 6 wherein one of $R_1$ is 4-chloro, and Q is hydroxy, said compound being 5-(4-chlorophenyl-phenylmethyl)-picolinic acid.

8. The compound of claim 6 wherein one of $R_1$ is 2-chloro, and Q is hydroxy, said compound being 5-(2-chlorophenyl-phenylmethyl)-picolinic acid.

9. A compound of claim 2 wherein R and $R_4$ are hydrogen and each $R_1$ is a halogen.

10. The compound of claim 9 wherein each $R_1$ is 4-chloro and Q is hydroxy, said compound being 5-[bis-(4-chlorophenyl)]methyl-picolinic acid.

11. A compound of claim 2 wherein R is an $R_1$-substituted diphenylmethyl group and $R_4$ being hydrogen.

12. The compound of claim 11 wherein each $R_1$ is hydrogen and Q is hydroxy, said compound being 3,5-[bis-(diphenylmethyl)]-picolinic acid.

13. A compound of claim 3 wherein $R_4$ is hydrogen.

14. The compound of claim 13 wherein each $R_1$ is hydrogen and Q is hydroxy, said compound being 4-(diphenylmethyl)picolinic acid.

15. A compound of claim 3 wherein each $R_1$ is hydrogen.

16. A compound of claim 15 wherein Q is hydroxy and $R_4$ is lower alkyl.

17. The compound of claim 16 wherein $R_4$ is ethyl, said compound being 4-(1,1-diphenylpropyl)-picolinic acid.

18. A diethanolamine salt of a compound of claim 1.

19. A compound of claim 18, said compound being 5-(4-chlorophenyl-phenylmethyl)-picolinic acid diethanolamine salt.

20. A piperazine salt of a compound of claim 1.

21. A compound of claim 20, said compound being 5-[bis-(4-chlorophenyl)-methyl]-picolinic acid piperazine salt.

22. A method of eliciting an anti-acne effect which comprises topically administering a therapeutically effective quantity of a compound of the formula:

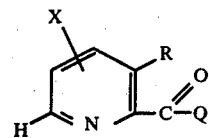

and the pharmaceutically acceptable salts thereof wherein X is a diphenylmethyl group having the structural formula:

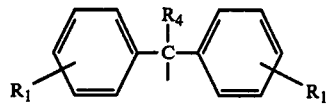

wherein $R_4$ is a member of the group consisting of hydrogen and lower alkyl; each $R_1$ is a member of the group consisting of hydrogen, halogen, hydroxy, alkyl, cycloalkyl, alkoxy, cycloalkoxy, trifluoromethyl and phenyl; Q is a member selected from the group consisting of hydroxy, alkoxy and glyceryl; R is a member of the group consisting of hydrogen, lower alkyl and X1, X1 being defined the same as X; wherein the alkyl, cycloalkyl, alkoxy and cycloalkoxy groups have up to 12 carbon atoms, the lower alkyl groups having 1 to 6 carbon atoms, said alkyl, lower alkyl and alkoxy groups including straight chain and branched chain hydrocarbyl groups; with the proviso that when R is other than hydrogen, X must be located at the 5-position of the pyridine ring.

* * * * *